United States Patent
Rosenberg

(10) Patent No.: US 9,333,377 B2
(45) Date of Patent: May 10, 2016

(54) APPLICATOR FOR SKIN TREATEMENT WITH AUTOMATIC REGULATION OF SKIN PROTRUSION MAGNITUDE

(75) Inventor: Avner Rosenberg, Bet Shearim (IL)

(73) Assignee: SYNERON MEDICAL LTD, Yoqneam Illit (IL)

(*) Notice: Subject to any disclaimer, the term of this patent is extended or adjusted under 35 U.S.C. 154(b) by 904 days.

(21) Appl. No.: 13/443,752

(22) Filed: Apr. 10, 2012

(65) Prior Publication Data

US 2012/0197242 A1    Aug. 2, 2012

Related U.S. Application Data

(62) Division of application No. 12/503,834, filed on Jul. 15, 2009.

(60) Provisional application No. 61/081,110, filed on Jul. 16, 2008.

(51) Int. Cl.
| | | |
|---|---|---|
| *A61H 1/00* | (2006.01) |
| *A61N 7/00* | (2006.01) |
| *A61B 18/14* | (2006.01) |
| *A61B 17/00* | (2006.01) |
| *A61B 17/30* | (2006.01) |
| *A61B 18/00* | (2006.01) |

(52) U.S. Cl.
CPC . *A61N 7/00* (2013.01); *A61B 18/14* (2013.01); *A61B 2017/00057* (2013.01); *A61B 2017/308* (2013.01); *A61B 2018/00011* (2013.01); *A61B 2018/00452* (2013.01); *A61B 2018/00994* (2013.01)

(58) Field of Classification Search
CPC ............................. A61N 7/00; A61H 23/0245
See application file for complete search history.

(56) References Cited

U.S. PATENT DOCUMENTS

| | | | | |
|---|---|---|---|---|
| 2,088,780 A | * | 8/1937 | Follese | 601/105 |
| 4,787,886 A | * | 11/1988 | Cosman | 604/9 |
| 6,544,259 B1 | * | 4/2003 | Tsaliovich | 606/36 |
| 6,662,054 B2 | * | 12/2003 | Kreindel et al. | 607/101 |
| 2006/0184024 A1 | * | 8/2006 | Da Silva et al. | 600/438 |
| 2006/0259102 A1 | * | 11/2006 | Slatkine | 607/88 |
| 2007/0179482 A1 | * | 8/2007 | Anderson | 606/9 |
| 2008/0051680 A1 | * | 2/2008 | Luebcke | 601/2 |

* cited by examiner

*Primary Examiner* — Tse Chen
*Assistant Examiner* — Hien Nguyen
(74) *Attorney, Agent, or Firm* — Smith Tempel Blaha LLC; Gregory Scott Smith

(57) ABSTRACT

Described is an applicator for RF, ultrasound, and light skin treatment. The applicator allows a protrusion of skin to be formed within a cavity and maintained for a desired time, enables good coupling of the treatment energy with the skin and avoids negative pressure adversely affecting the skin.

15 Claims, 6 Drawing Sheets

APPLICATOR FOR SKIN TREATEMENT WITH AUTOMATIC REGULATION OF SKIN PROTRUSION MAGNITUDE

CROSS-REFERENCE TO RELATED APPLICATIONS

This is a United States Non-provisional application for patent being filed under 35 USC 111 as a divisional application of and claiming priority to U.S. patent application Ser. No. 12/503,834 filed on Jul. 15, 2009 and bearing the title of APPLICATOR FOR SKIN TREATMENT WITH AUTOMATIC REGULATION OF SKIN PROTRUSION MAGNITUDE, which application claims the priority to the United States Provisional application for patent that was filed on Jul. 16, 2008 and assigned Ser. No. 61/081,110. This application incorporates by reference U.S. Pat. No. 6,889,090, United States Patent Publication No. 2007/0038156 and U.S. patent application Ser. No. 12/503,834.

TECHNICAL FIELD

The method and apparatus relate to non-invasive aesthetic treatment procedures and in particular to body shaping, skin treatment and other aesthetic treatments.

BACKGROUND

Body shaping, skin tightening and rejuvenation, collagen fibers contraction, removal of wrinkles, and other aesthetic skin treatments are popular and widely used in the field of cosmetic and appearance improvement procedures. The treatments are typically provided through the application of electromagnetic or acoustic energy to a target section of skin. In these treatment procedures, an applicator having an inner cavity or vacuum chamber is typically applied to the skin of a subject such that the section of the skin to be treated is pulled up or drawn into the vacuum chamber forming a skin fold that will be termed as skin protrusion. The electromagnetic energy, such as Radio Frequency (RF), or acoustic energy, such as ultrasound, is applied to one or more sides of the protrusion to perform a desired skin/tissue effect in the skin/tissue between the electrodes or between ultrasound transducers. After the treatment, the skin is again straightened or the protrusion is relaxed and the desired skin effect such as, for example contraction of collagen fibers or destruction of adipose tissue by the electromagnetic or acoustic energy, is realized.

The generation of the skin protrusion includes multiple advantages, one such being that it allows all or portions of the skin to be treated by rapidly conforming to the shape of the applicator and preventing undesired movement of the applicator during the treatment. Formation of the protrusion and negative pressure in the cavity is also necessary to stabilize and temporarily attach energy emitting contact surfaces to the skin. Properly attached electrodes couple larger portions of RF or ultrasound and increase the desired treatment effects, reduce the number of treatments required to reach the desired effect, and improve the success confidence of the treated subject. However, to ensure proper contact with the skin, the vacuum that is applied to the skin should be strong enough to form and maintain the protrusion. However, the application of sufficient vacuum force to provide the desired contact has some negative effects on the skin. These negative effects can include, among other things, leaving endemic bruising spots on the skin, causing pain to the treated subject during the procedure and following, and requiring extended post-treatment recovery periods.

The vacuum chamber or cavity used for protrusion formation has a relatively large size but, the skin drawn inside may occupy only a section of the cavity. The pump that delivers vacuum or negative pressure into the chamber should be a relatively large pump enabling rapid air evacuation from the cavity, protrusion formation and maintaining of the protrusion for at least the time of treatment. These requirements unfortunately increase the cost of the equipment used for different skin treatment procedures because, there is variability in the skin properties between different subjects. In addition, because of this, low-level vacuum pressure or force is sufficient for generation of the required protrusion for some treated subjects. However, other subjects may require a substantially higher level of vacuum force. It is a common practice of the caregiver or operator to manually adjust or vary the vacuum level, until he or she finds the optimal level, which is sufficient for the treatment of the skin and does not cause painful sensations. This optimal vacuum level varies from one subject to the other, sometimes there is no such optimal level, and the treatment is either painful or inefficient.

It would be desirable to have an applicator that would allow a protrusion to be formed and maintained for a desired time with good coupling to the energy emitting surfaces, without adversely affecting the skin or causing pain to the treated subject.

BRIEF SUMMARY

Described is an applicator for RF, ultrasound, and light skin treatment. The applicator includes a cavity operatively configured to receive into it a segment of skin to be configured as a protrusion and a valve. The cavity communicates with a source of negative pressure. The protrusion applies pressure to the valve and displaces the valve in the cavity. The valve displacement regulates the negative pressure in the cavity.

RF energy, ultrasound or light energy may be applied to the skin protrusion at different overlapping and none overlapping periods to cause the desired treatment effect.

The applicator allows a protrusion to be formed and maintained for a desired time, enables good coupling of the treatment energy with the skin and avoids negative pressure adversely affecting the skin.

BRIEF DESCRIPTION OF THE DRAWINGS

The applicator and method of the applicator use are particularly indicated and distinctly claimed in the concluding portion of the specification. The applicator and the method, however, both as to organization and method of operation, may best be understood by reference to the following detailed description when read with the accompanied drawings, in which like reference characters refer to the same parts throughout the different views. The drawings are not necessarily to scale, emphasis instead being placed upon illustrating the principles of the method.

DETAILED DESCRIPTION OF EXEMPLARY EMBODIMENTS

In the following detailed description, for purposes of explanation, numerous specific details are set forth in order to provide a thorough understanding of the present applicator, principles of the applicator operation and method of using the applicator. It will be apparent, however, that the present applicator and method may be practiced without these specific details. In this regard, directional terminology, such as "up," "down," "front," "back," etc., is used with reference to the orientation of the Figure(s) being described. Because components of embodiments of the present invention can be positioned in a number of different orientations, the directional terminology is used for purposes of illustration and is in no way limiting.

Figure 1:
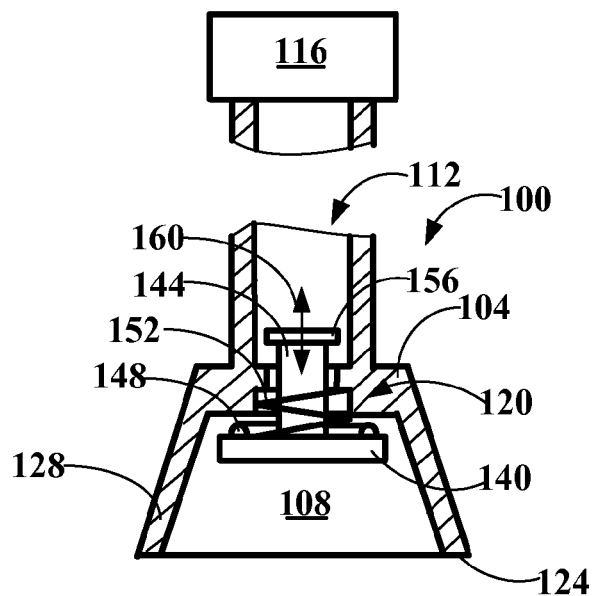
FIG. 1 is a schematic illustration of an exemplary embodiment of the present applicator.

Reference is made to FIG. 1, which is a schematic illustration of an exemplary embodiment of the present applicator. Applicator 100 represents a housing 104 made of metal or plastic material with a hollow cavity 108 formed inside of housing 104. Cavity 108 communicates through first end 112 with a source of negative pressure 116 and a valve 120 located in the interior of cavity 108 and controlling communication between the cavity and the source of negative pressure. A flexible hose (not shown) may connect between first end 112 of applicator 100 and source of negative pressure such as for example, a vacuum pump 116.

A rim 124 terminates the second end of applicator 100. Rim 124 may have a thickness similar to the walls 128 of applicator 100 housing 104; it may terminate by a gasket, or have a surface (FIG. 3) substantially larger than walls 128. Valve 120 is an assembly of a plate 140, guide 144, 0-ring type gasket 148, spring 152 and a stopper disk 156. Other valve structures such as two mated conical or spherical surfaces are possible. Valve 120 has a freedom of linear movement in the axial direction as indicated by arrow 160. The clearance between guide 144 and applicator housing 104 should be selected such as to enable easy evacuation of air from cavity 108 and would typically be about 0.2 cm2.

Figure 2A:
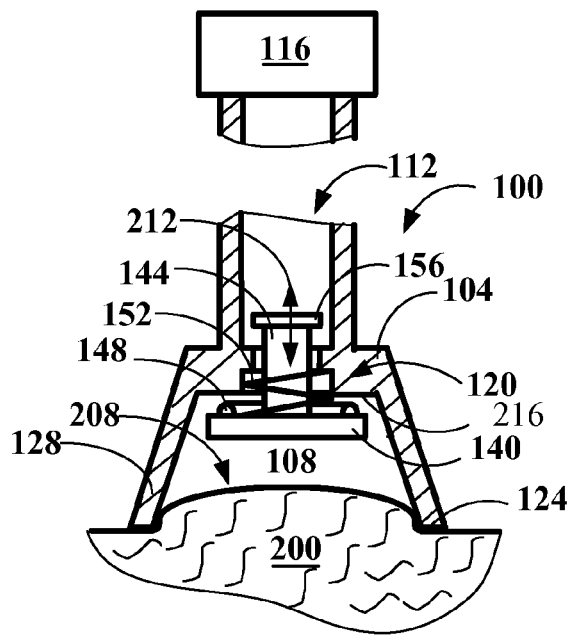
FIGS. 2A and 2B, collectively referred to as FIG. 2, are schematic illustrations showing the operation of an exemplary embodiment of the present applicator.
Figure 2B:
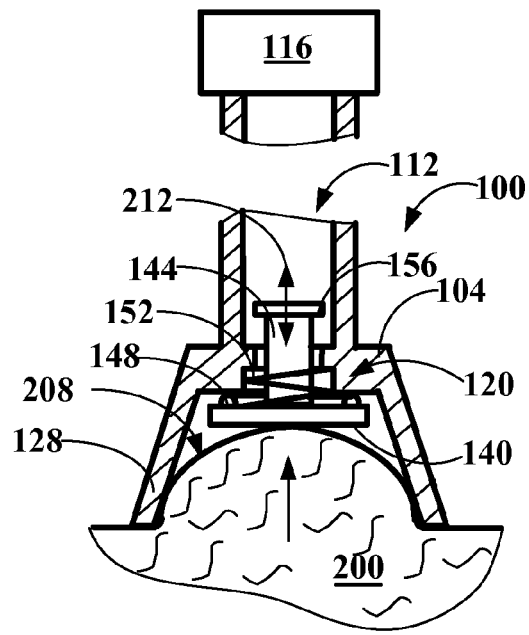

FIGS. 2A and 2B, collectively referred to as FIG. 2 are schematic illustrations showing the operation of an exemplary embodiment of the present applicator. In operation, applicator 100 is placed on the section of the skin to be treated such that rim 124 contacts skin 200 and cavity 108 becomes enclosed between skin 200, applicator walls 128 and plate 140 of valve 120. (As used in the present disclosure the terms "skin" and "tissue" have the same meaning.) In some embodiments, a gasket-improving rim 124 with skin 200 contacts may be used. Source of negative pressure 116 evacuates air from cavity 108. The negative pressure in cavity 108 pulls or draws skin 200 into the cavity and forms a skin protrusion 208 (FIG. 2A).

Pump 116 continues to operate and protrusion 208 expands further occupying almost all volume of cavity 108. As protrusion 208 expands it contacts plate 140 of valve 120, displaces or pushes the plate, and components of valve 120 associated with it in the direction indicated by arrow 212 (FIG. 2B) such that gasket 148 contacts the inner surface 216 of applicator housing 104. Additional increase in the magnitude or volume of protrusion 208 increases the positive pressure applied to plate 140 and O-ring type gasket 148 mounted on it. This pressure further displaces plate 140 and attaches gasket 148 to the surface 216 of cavity 108. Gasket 148 temporarily seals cavity 108 and establishes the volume or magnitude of protrusion 208 that fills-in cavity 108. Different skin treatments, aesthetic and non-aesthetic, may be applied to protrusion 208.

As the time passes, air gradually leaks into cavity 108 of applicator 100. The value of the negative pressure diminishes, and protrusion 208 reduces its magnitude or volume and recedes. Forces generated by spring 152 maintain permanent contact of plate 140 with protrusion 208 and return plate 140 and associated with plate 140, parts of valve 120 to the original location or to a section of the stroke. Spring 152 develops relatively gentle force that pushes down plate 140. For example, if the pump 116 generates a negative pressure of 0.6 Bar and the cross section of the valve is 0.2 cm2, the force would be 1.2N. Such gentle pressure required for formation of the protrusion is relatively low and does not generate adverse effects in or on the skin.

Valve 120 operated by positive pressure developed by skin protrusion 208 and spring 152 forces, acts like an ON-OFF switch enabling or disabling communication with pump 116. Actually, protrusion 208 automatically regulates its magnitude by regulating the level of the negative pressure developed by pump 116, forcing protrusion shape and volume optimally for the desired treatment, and enabling firm contact to the surfaces of cavity walls. Excessive negative pressure values are automatically avoided and no damage, pain or other adverse effects are inflicted to the treated skin section. Spring 152 ensures the return path of valve 120 when the action of pump 116 is discontinued, locating valve 120 into a position suitable for the next treatment cycle and/or translation to a new skin section. Thus, the valve operates as a protrusion magnitude detector by switching off the negative pressure when the protrusion reaches a desired or threshold value, which moves the valve to a position to throw the switch.

Figure 3A:
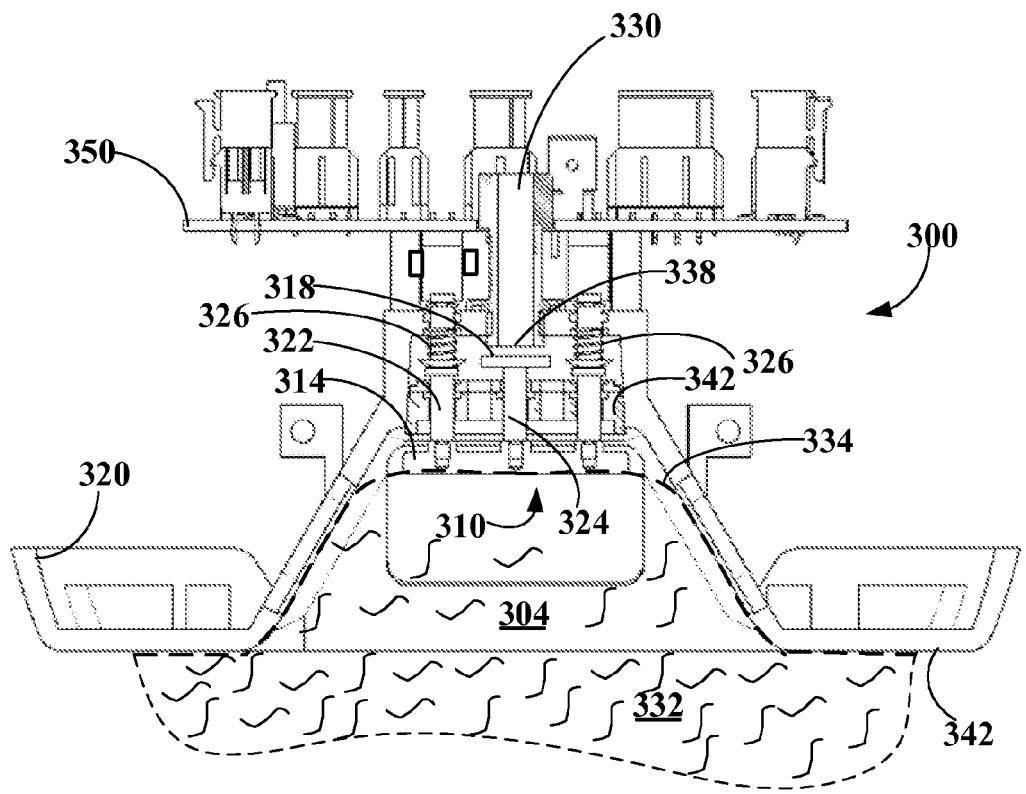
FIGS. 3A and 3B, collectively referred to as FIG. 3, are schematic illustrations showing operation of another exemplary embodiment of the present applicator.
Figure 3B:
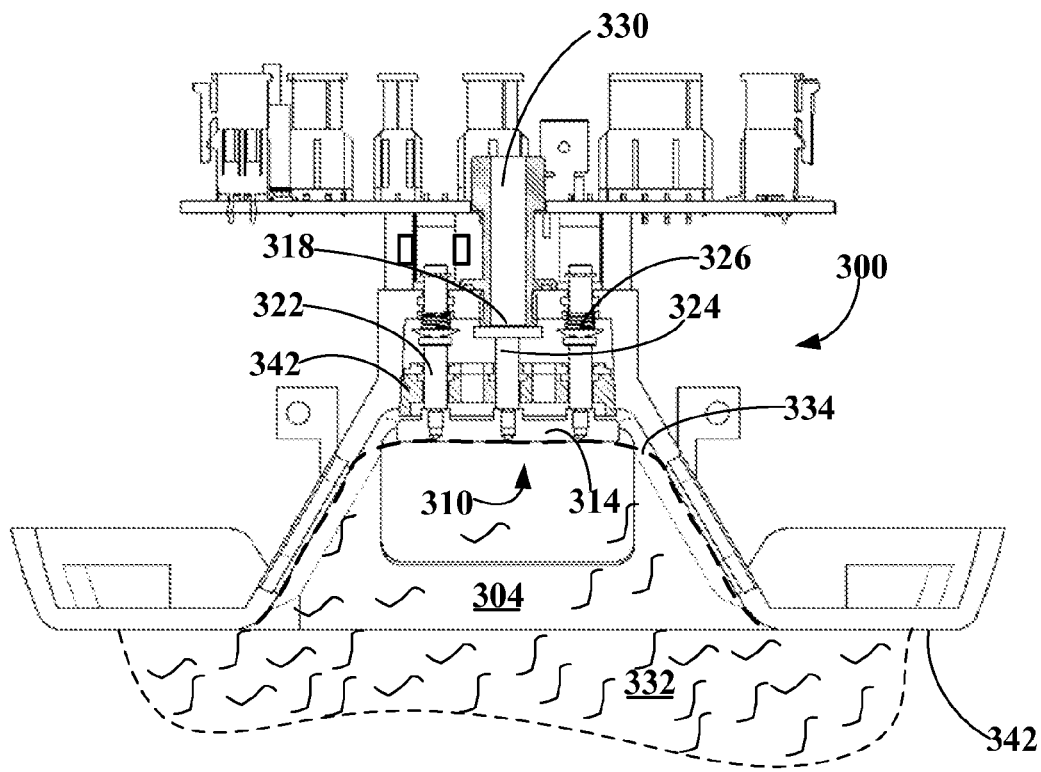

FIGS. 3A and 3B, collectively referred to as FIG. 3 are schematic illustrations showing operation of another exemplary embodiment of the present applicator for skin treatment. The size of the applicator, among others, depends on the desired size of the skin segment to be treated and the ability to generate and maintain a proper skin protrusion magnitude. Accordingly, the applicator may have a larger plate 314 or a number of guides 322 included in the valve assembly. FIG. 3A illustrates an applicator 300 having valve 310 consisting of plate 314, flat or other suitable type gasket 318, guides 322, a pusher 324, and springs 326. In an alternative embodiment, gasket 318 may be mounted on surface 338. Channel 330 enables communication with a negative pressure source (not shown). Two or more guides 322 may be required to avoid plate 314 skew and enable rapid and uniform contact of gasket 318 with surface 338 of housing 320 of applicator 300 or channel 330. Operation of applicator 300 is similar to the operation of applicator 100. When the source of negative pressure (not shown) is operative, it forms in cavity 304 a skin protrusion shown by phantom line 334. Protrusion 334 pushes up plate 314 of valve 310 regulating the level of vacuum in the cavity and the protrusion 334 magnitude.

FIG. 3B illustrates applicator 300 in a state where protrusion 334 has reached the desired magnitude. Gasket 318 closes vacuum passage 330. Protrusion 334 maintains its magnitude for a certain time until air leakage into cavity 304 enables forces generated by springs 326 that maintain a permanent contact of plate 314 with protrusion 334 to push down plate 314 and parts of valve 310 associated with it. This enables communication of cavity 304 with the source of vacuum (not shown). Applicator 300 possesses a relatively large rim 342 enabling easy applicator over the surface of skin/tissue 332 displacement and firm contact with the skin/tissue.

It is known that aesthetic and medical skin treatments are usually accompanied by application of gel to the treated skin surface. The purpose of the gel application may be for the improvement of electrical contact with the skin, improvement of ultrasound to skin coupling, and easier translation of the applicator over the skin. The application of the vacuum force may result in sucking the applied skin gel into the vacuum system. The gel may become an obstacle to proper vacuum system operation it may deposit the gel in undesired places and applicator components. The gel hardens with time, and even may damage the vacuum pump. Applicator 300 is equipped by a gel guard 342 with dimensions tightly fitted to the applicator 300 inner cross section dimensions. In one embodiment, gel guard 342 is a reusable part that should be cleaned from time to time as gel accumulates on it. In another embodiment, gel guard 342 is an easily exchangeable disposable part. The disposable gel guard 342 may include guides 322 and pusher 324 with stopper disk 318, further simplifying gel guard replacement. It should be clear that other applicator constructions are possible, including more than two guides, different valve and gasket locations and structures.

Figure 4:
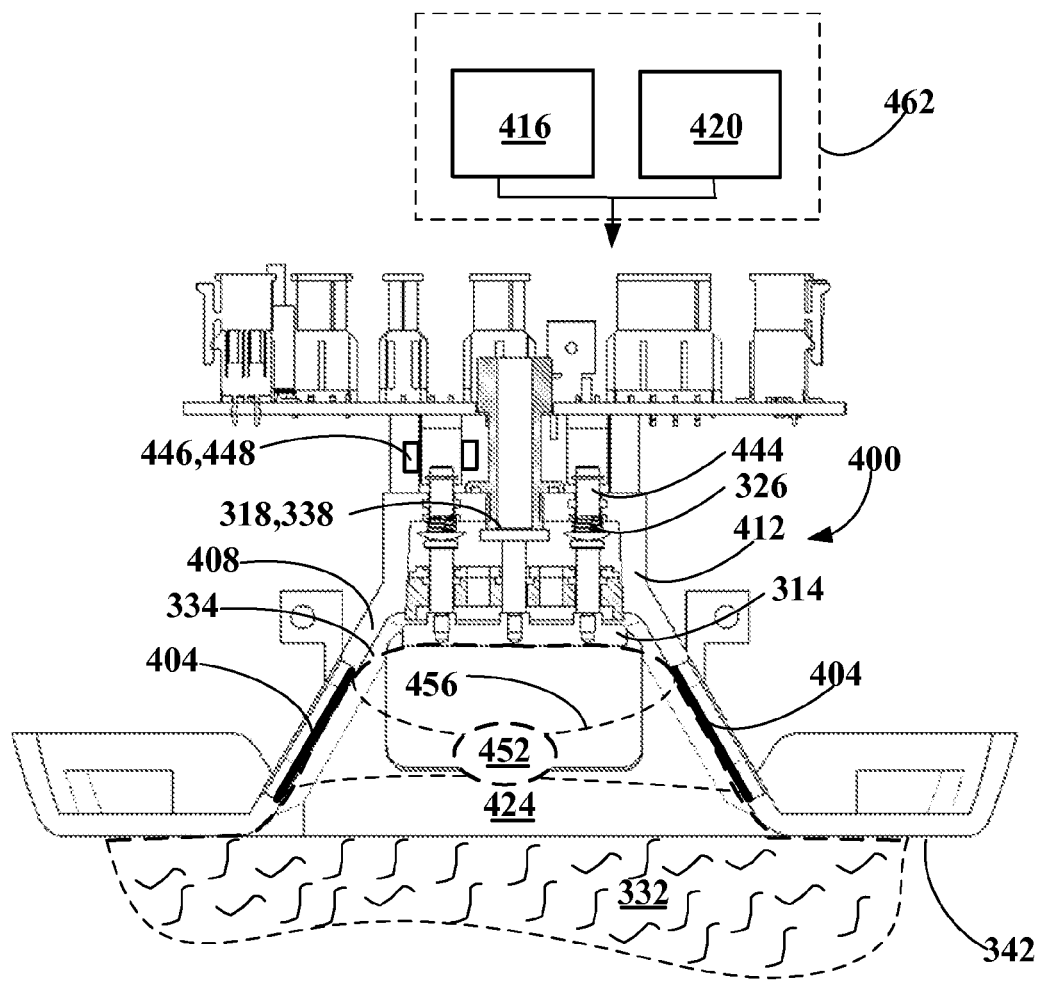
FIG. 4 is a schematic illustration of an exemplary embodiment of the present applicator configured to apply RF energy to a section of the skin formed as a protrusion.

One of the applications of the present applicator is for RF skin treatment. FIG. 4 is a schematic illustration of an exemplary embodiment of the present applicator configured to apply RF energy to a skin protrusion. Applicator 400 includes one or more RF electrodes 404 that are built-in to walls 408 of housing 412, or located close to walls 408 of the housing 412. An RF energy generator 416 provides RF energy to electrodes 404. The RF energy would typically have a frequency of 0.5-10 MHz and energy of 0.5-50.0 J/cm2 and it may be introduced into the skin in a pulsed or continuous mode.

Safety of the application of RF to a subject's skin is aparamount requirement in every aesthetic and medical RF based treatment. Firm contact between electrodes 404 and protrusion 334 ensure good energy to skin transfer, avoids formation of hot spots on the electrodes, and other adverse effects. Such contact conditions exist only when skin protrusion 334 completely fills cavity 424. Sensing of protrusion magnitude (or status) may provide feedback to controller 462 that controls RF generator 416 supplying RF to electrodes 404. Such "protrusion detector (or sensor)" sends the control system 462 a signal when the tissue fills the cavity into the tissue as required for safe energy application. In one embodiment, shown in FIG. 4, the protrusion sensor is based on an optical path between an LED 446 and light detector 448 with the continuity of the pass being interrupted by pin 444 when plate 314 is pushed up by protrusion 334. There is also a possibility of using a mechanical, resistive, capacitive, inductive sensor or any other type of sensor that is suitable for the direct or auxiliary detection of the protrusion magnitude. An optical sensor may be placed inside cavity 424 as well as a skin laxity sensor.

Pump 420 generates negative pressure of about −0.1 bar to −0.9 bars, in cavity 424. The negative pressure or vacuum draws skin or tissue 332 into cavity 424 forming a skin protrusion 334. As skin protrusion 334 growths, it occupies a larger volume of cavity 424, and spreads in a uniform way inside the cavity. The protrusion spreading enables firm contact of skin 332 with electrodes 404. Protrusion 334 pushes plate 314 up such that gasket 318 contacts surface 338 of the vacuum communication channel disabling vacuum communication with pump 420. When the negative pressure in cavity 424 drops down, for example, because of air leakage, protrusion 334 recedes or diminishes. Springs 326 push plate 314 and gasket 318 down, away from surface 338 and enable vacuum pump 420 to communicate once again with cavity 424 and evacuate the air from it.

When firm contact between skin protrusion 334 and electrodes 404 is established, controller 462 switches ON RF generator 416 and RF energy is supplied to target volume 452 of skin 332. Phantom lines 456 illustrate schematically RF induced current flow in skin protrusion 334. This current heats target tissue volume 452 and enables the desired treatment effect, which may be body shaping, skin tightening and rejuvenation, contraction of collagen fibers, removal of wrinkles and other aesthetic skin treatment effects. Proper contact between electrodes 404 and skin protrusion 334 may be detected during the treatment by monitoring skin impedance between electrodes 404 as disclosed in the U.S. Pat. No. 6,889,090 to the same assignee. The lower the skin impedance at the beginning of treatment, the better is the contact between electrodes 404 and skin 432 forming protrusion 334.

Increasing skin temperature by RF induced currents, leads to a change in impedance. Monitoring the skin impedance allows the temperature distribution in the skin to be followed so that the parameters of the treatment may be determined, enabling treatment optimization. Such parameters may include, for example, the time RF is applied to the skin, the pulse duration of the RF energy, the frequency of the RF energy, the power of the RF energy, the delay time between cooling the skin and the application of the RF energy.

Other known impedance monitoring methods may also be applied. Applicator 400 may contain additional devices for temperature monitoring, skin and electrodes cooling, illumination devices for illuminating the treated skin section, and others, as may be required by a particular skin treatment. RF generator 416, vacuum pump 420 and other control and auxiliary units such as a cooling fluid pump, impedance measurement circuit, wiring and tubing not shown for the simplicity of explanation, may be placed in a common controller 462 packaging.

It should be noted that the protrusion sensor can be for other purposes rather then simply as a safety feature preventing undesired energy application to a partial protrusion. For instance, the sensor, as will be explained below, can be used to establish tissue properties and in particular tissue laxity, by measuring the time between the start of vacuum and the time when protrusion reaches its desired magnitude. (The terms "tissue flexibility" and "tissue laxity" occasionally used through the disclosure have the same meaning.)

Figure 5:
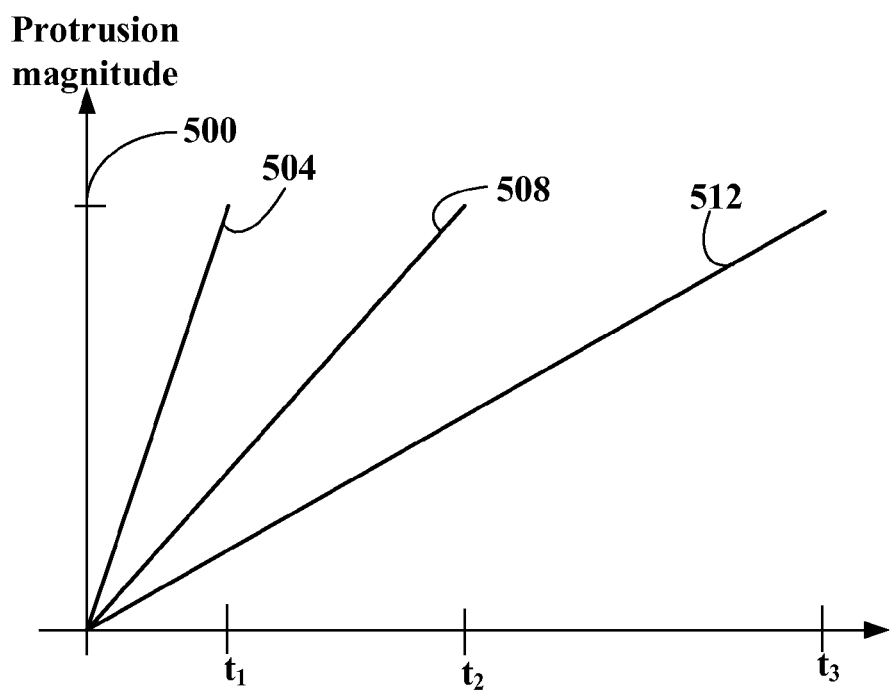
FIG. 5 is a schematic illustration of the protrusion formation time for tissues with different laxities.

It has been experimentally discovered that the time of protrusion formation is a function of the treated subject tissue laxity and structure. FIG. 5 is a schematic illustration of the protrusion formation time for tissues with different laxities. Numeral 500 marks the protrusion magnitude desired for a particular treatment. Under all other equal condition, line 504 and time t1 mark protrusion formation for a relatively high laxity tissue. Lines 508 and 512 mark protrusion formation times t2 and t3 for stiffer (more rigid) tissues than line 504 mark, with line 512 and t3 marking the stiffest tissue. For example, protrusion formation time for high laxity tissue is about 20 milliseconds to 200 milliseconds. Protrusion formation time for stiff (rigid) tissue is about 1200 millisecond to 2000 millisecond. Knowledge of the protrusion formation time enables selection of the appropriate tissue treatment parameters for each type. The treatment parameters may be set manually, based on the protrusion formation time, or automatically by including in the controller a feedback loop reading the time from LED 446 and sensor 448 (FIG. 4) and using at least part of the feedback to establish the type of tissue and the tissue treatment parameters.

Tissue laxity may be a good indicator of the need to perform a tissue pretreatment procedure. Such procedure may be a massage or heat application to soften the treated tissue and make it more suitable for the treatment itself. Thus the method disclosed provides a diagnostic tool for determination of tissue stiffness and indication of the treatment parameters most suitable for the particular tissue.

Figure 6A:
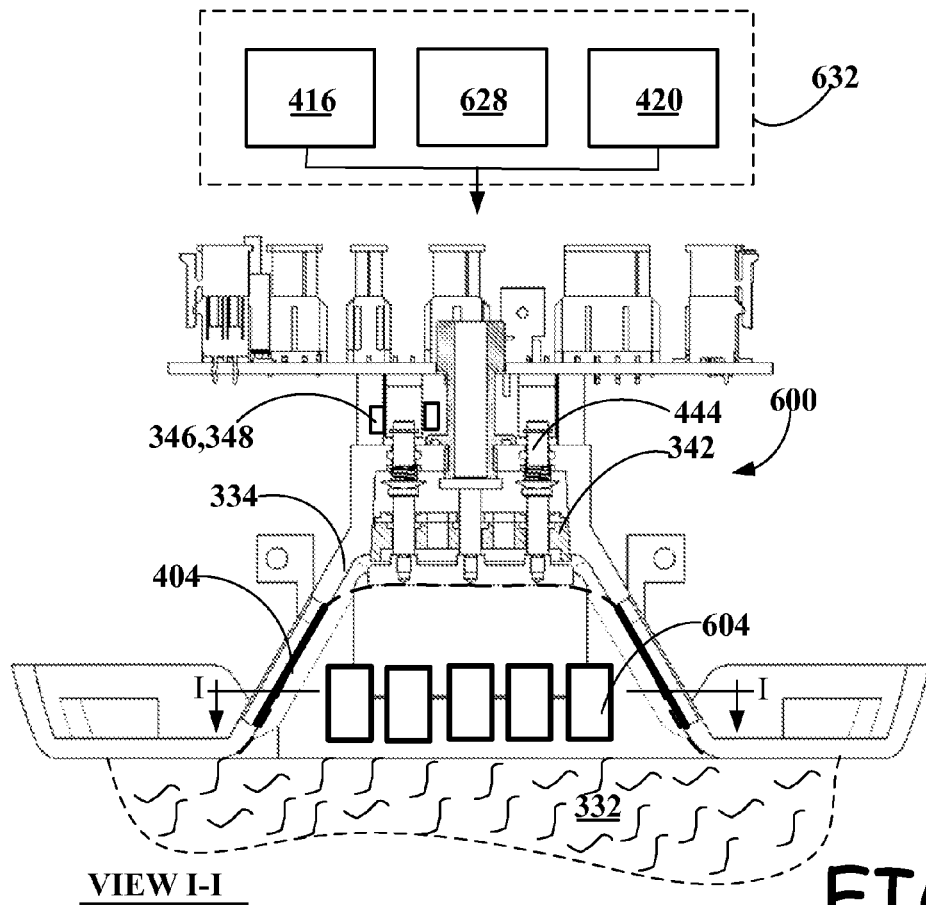
FIGS. 6A and 6B, collectively referred to as FIG. 6, are schematic illustrations of an exemplary embodiment of the present applicator configured to apply RF and ultrasound energy to a section of the skin formed as a protrusion.
Figure 6B:
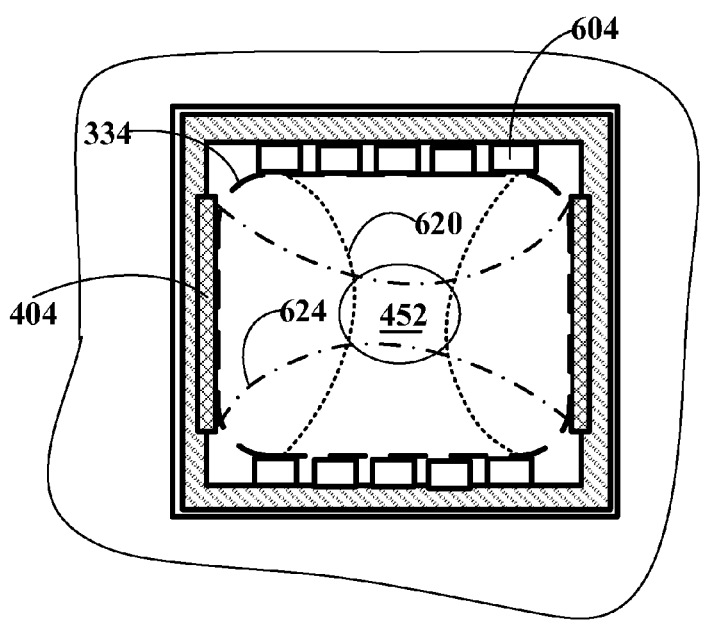

FIGS. 6A and 6B, collectively referred to as FIG. 6, are schematic illustrations of an exemplary embodiment of the present applicator configured to apply RF and ultrasound energy to a section of the skin. Applicator 600 (FIG. 6A) is similar to applicator 400 and includes, in addition, one or more ultrasound transducers 604. Transducers 604 may be of conventional type or phased array transducers. Transducers 604 may be located on one or both sides of applicator 600 and typically, as disclosed in United States Patent Publication No. 2007/0038156 to the same assignee, incorporated here in its entirety and are focused to emit energy into the same target treatment volume 452 (FIG. 6B) located between RF electrodes 404 and affected by the US energy. Applicator 600 includes a LED 446 and skin protrusion detector 448 and may contain devices for temperature monitoring, skin and electrode cooling, illumination devices for illuminating the treated skin section, and others, as may be required by a particular skin treatment.

RF generator 420 and ultrasound generator 628 provide energy to respective electrodes and transducers. Vacuum pump 416 generates negative pressure forming skin protrusion 334. Sensing of skin protrusion magnitude (or status) may provide feedback to controller 632 that controls RF generator 420 supplying RF to electrodes 404 and ultrasound generator 628 supplying ultrasound energy to transducers 604. In operation such "protrusion detector (or sensor)" sends the control system 632 a signal when the tissue fills-in the cavity as required for safe energy application into the tissue. The protrusion sensor signal may be used to switch ON and OFF the RF generator 420 and ultrasound generator 628. These and other control and auxiliary units such as a cooling fluid pump, wiring and tubing not shown for the simplicity of explanation, may be placed in a common controller packaging 632.

FIG. 6B is a cross section of applicator 600 illustrating location of RF electrodes 404, ultrasound transducers 604, and acoustic field lines 620 generated by transducers 604 and RF induced current lines 624. Circle 630 schematically shows the target volume heated by the ultrasound and RF.

The RF and ultrasound energy are applied for short time duration, as a pulse or a train of pulses (or several pulses), in order to reduce loss of heat from the ultrasound heated focal tissue volumes by conduction or convection. RF and ultrasound energies may be applied simultaneously or one delayed with respect to the other.

The temperature generated at the focal volumes by the RF and ultrasound energy sources and the time of heating are selected such that adequate heating of the focal volumes is obtained, while heating of surrounding tissues is minimal. Increased temperature of the focal volumes facilitated the mechanical action of ultrasound applied to the same volume and helps in achieving a substantial treatment effect.

A number of embodiments have been described. Nevertheless, it will be understood that various modifications may be made without departing from the spirit and scope of the method.

What is claimed is:

1. An applicator for skin treatment, said applicator comprising:
    a housing defining a cavity for receiving a section of skin to be configured as a protrusion, said cavity housing communicating with a vacuum source to provide negative pressure within the cavity, and a valve located in the interior of said cavity and being configured to control communication with said source of negative pressure; and
    one or more RF electrodes communicating with an RF energy generator; and
wherein said valve also comprises:
    a plate coupled with at least one guide, said plate configured to be displaced by positive pressure applied thereto by the protrusion of skin when drawn into the cavity;
    a gasket associated with the plate such at as the protrusion of skin is drawn into the cavity, the gasket contacts an inner surface of the cavity thereby sealing the cavity and disabling negative pressure from the vacuum source; and
    a spring configured to return the displaced plate towards its non-displaced position when the protrusion of skin recedes from the cavity due to air leaking into the cavity, whereby enabling negative pressure from the vacuum source.

2. The applicator according to claim 1, further comprising at least one ultrasound transducer.

3. The applicator according to claim 2, wherein said ultrasound transducer communicates with an ultrasound energy generator providing ultrasound energy to said transducer.

4. The applicator according to claim 2, wherein said ultrasound transducer is at least one of a group consisting of conventional or phased array transducers.

5. The applicator according to claim 1, further comprising at least one source of illumination.

6. The applicator according to claim 1, further comprising a disposable gel guard.

7. A method of skin treatment, said method comprising:
    placing an applicator onto a section of skin, the applicator defining a cavity and, the cavity being configured to receive at least a portion of the section of the skin, and a valve located in the interior of said cavity and configured to control communication with a source of negative pressure, and at least one RF electrode communicating with an RF energy generator;
    forming a skin protrusion by drawing at least a portion of said section of skin into the cavity by the application of negative pressure and wherein the protrusion regulates its magnitude by contacting and applying positive pressure to the valve such that the valve is displaced by the positive pressure of skin protrusion pressing displacing plate and gasket and forcing them against the valve to create a seal, whereby disabling negative pressure from a vacuum source;
    applying RF energy to said skin protrusion; and
    applying spring pressure to the plate to cause the plate to move towards a non-displaced position when the protrusion of skin recedes from the cavity due to air leaking into the cavity, whereby enabling negative pressure from the vacuum source.

8. The method according to claim 7, wherein a positive pressure applied by the skin protrusion to the valve disables the communication with said source of negative pressure.

9. The method according to claim 7, wherein the RF energy is applied to said skin protrusion in a pulsed or continuous mode.

10. The method according to claim 7, wherein the RF energy applied to said protrusion has power and frequency sufficient to cause a desired treatment effect.

11. The method according to claim 7, further comprising the step of applying ultrasound energy to said skin protrusion.

12. The method according to claim 11, wherein the step of applying ultrasound energy further comprising applying ultrasound energy to said skin protrusion before or simultaneously with said RF energy.

13. The method according to claim 11, further comprising the step of sensing the magnitude of the skin protrusion and applying the a signal to switch ON or OFF the application of at least one of the RF or the ultrasound based on the sensed magnitude.

14. The method according to claim 7, wherein the step of forming a skin protrusion further comprises actuating the valve so as to control the value of said negative pressure in such a manner to reduce the generation of adverse effects on the skin.

15. The method according to claim 7, further comprising the steps of:
   applying a gel to the treated section of the skin,
   and preventing penetration of gel into a vacuum system by attaching a disposable gel guard to the applicator.

\* \* \* \* \*